US00PP30205P2

(12) United States Plant Patent
van den Hoogen

(10) Patent No.: US PP30,205 P2
(45) Date of Patent: Feb. 12, 2019

(54) ***MONARDA* PLANT NAMED 'ALLVIN'**

(50) Latin Name: *Monarda didyma*
Varietal Denomination: Allvin

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 15/732,570

(22) Filed: Nov. 29, 2017

(51) Int. Cl.
*A01H 5/02* (2018.01)

(52) U.S. Cl.
USPC ..... Plt./455

(58) Field of Classification Search
USPC ..... Plt./455
See application file for complete search history.

(56) References Cited

PUBLICATIONS

Pluto Plant Variety Database Aug. 28, 2018.*

* cited by examiner

*Primary Examiner* — Annette H Para
(74) *Attorney, Agent, or Firm* — C. A. Whealy

(57) ABSTRACT

A new and distinct cultivar of *Monarda* plant named 'Allvin', characterized by its upright plant habit; dark green-colored leaves; freely flowering habit; rich purple-colored flowers; long flowering period; and good postproduction longevity.

2 Drawing Sheets

Botanical designation: *Monarda didyma.*
Cultivar denomination: 'ALLVIN'.

BACKGROUND OF THE INVENTION

The present invention relates to a new and distinct cultivar of *Monarda* plant, botanically known as *Monarda didyma*, typically grown as a cut flower and hereinafter referred to by the name 'Allvin'.

The new *Monarda* plant is a product of a planned breeding program conducted by the Inventor in Cuijk, The Netherlands. The objective of the breeding program is to create new strong *Monarda* plants with attractive flowers and good postproduction longevity.

The new *Monarda* plant originated from an open-pollination in September, 2013 of a proprietary selection of *Monarda didyma* identified as code number 28-2013-56-12, not patented, as the female, or seed, parent with an unknown selection of *Monarda didyma*, as the male, or pollen, parent. The new *Monarda* plant was discovered and selected by the Inventor as a single flowering plant from within the progeny of the stated open-pollination grown in a controlled nursery environment in Cuijk, The Netherlands in September, 2014.

Asexual reproduction of the new *Monarda* plant by terminal cuttings in Cuijk, The Netherlands, since April, 2015 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvin'. These characteristics in combination distinguish as a new and distinct *Monarda* plant:

1. Upright plant habit.
2. Dark green-colored leaves.
3. Freely flowering habit.
4. Rich purple-colored flowers.
5. Long flowering period.
6. Good postproduction longevity.

Plants of the new *Monarda* differ primarily from plants of the female parent selection in leaf texture as leaves of plants of the new *Monarda* are less pubescent than leaves of plants of the female parent selection.

Plants of the new *Monarda* can be compared to plants of *Monarda didyma* 'Allbell', disclosed in U.S. Plant Pat. No. 27,496. In side-by-side comparisons plants of the new *Monarda* differ from plants of 'Allbell' in the following characteristics:

1. Plants of the new *Monarda* have lighter green-colored leaves than plants of 'Allbell'.
2. Plants of the new *Monarda* have lighter green-colored stems than plants of 'Allbell'.
3. Plants of the new *Monarda* and 'Allbell' differ in flower color as plants of 'Allbell' have red purple-colored flowers.

BRIEF DESCRIPTION OF THE PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph on the first sheet is a side perspective view of a typical flowering plant of 'Allvin' grown in a 23-cm container.

The photograph at the top of the second sheet is a close-up view of the upper surface of a typical leaf of 'Allvin'.

The photograph at the bottom of the second sheet is a close-up view of typical inflorescences of 'Allvin'.

DETAILED BOTANICAL DESCRIPTION

The aforementioned photographs and following observations, measurements and values describe plants grown during September in an outdoor nursery in Cuijk, The Netherlands and under cultural practices typical of commercial *Monarda* production. During the production of the plants, day temperatures ranged from 15° C. to 32° C. and night temperatures ranged from 12° C. to 20° C. Plants were five months old when the photographs and the description were taken. In the detailed description, color references are made to The Royal Horticultural Society Colour Chart, 2015 Edition, except where general terms of ordinary dictionary significance are used.

Botanical classification: *Monarda didyma* 'Allvin'.

Parentage:

*Female, or seed, parent*.—Proprietary selection of *Monarda didyma* identified as code number 28-2013-56-12, not patented.

*Male, or pollen, parent*.—Unknown selection of *Monarda didyma*, not patented.

Propagation:

*Type cutting*.—By terminal cuttings.

*Time to initiate roots, summer*.—About 10 to 14 days at temperatures ranging from 12° C. to 30° C.

*Time to produce a rooted young plant, summer*.—About four to six weeks at temperatures ranging from 12° C. to 30° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; upright plant form; moderately vigorous to vigorous growth habit.

*Plant height, soil level to top of foliar plane*.—About 96 cm.

*Plant height, soil level to top of floral plane*.—About 104 cm.

*Plant width*.—About 67 cm.

*Lateral branch description*.—Branching habit: Freely basal branching habit with about 20 main stems, each main stem with about eight lateral branches. Length: About 44.4 cm. Diameter: About 4 mm. Internode length: About 7.8 cm. Strength: Strong. Aspect: Main stems, upright to about 40° from vertical; lateral branches, about 30° from main stem axis. Texture and luster: Moderately pubescent; slightly glossy. Color: Developing, close to 144B to 144C; fully developed, close to 144A; at the internodes, close to 144A tinged with close to 182B.

Leaf description:

*Arrangement*.—Opposite, simple.

*Length*.—About 8.7 cm.

*Width*.—About 4 cm.

*Shape*.—Ovate.

*Apex*.—Acuminate.

*Base*.—Short attenuate to obtuse.

*Margin*.—Serrate.

*Texture and luster, upper surface*.—Moderately pubescent; slightly glossy.

*Texture and luster, lower surface*.—Moderately pubescent; matte.

*Venation pattern*.—Pinnate.

*Fragrance*.—Fragrant; somewhat spicy, pleasant.

*Color*.—Developing leaves, upper surface: Close to 137B. Developing leaves, lower surface: Close to 143C. Fully expanded leaves, upper surface: Close to NN137A; venation, close to 148B. Fully expanded leaves, lower surface: Close to 147B; venation, close to 148C to 148D.

*Petioles*.—Length: About 1.6 cm. Diameter: About 2 mm. Strength: Strong. Texture and luster: Densely pubescent; slightly glossy. Color, upper surface: Close to 144A strongly tinged with close to N77B. Color, lower surface: Close to 144C.

Flower description:

*Flower form, arrangement and flowering habit*.—Single labiate flowers arranged in terminal globular spikes; flowers face upright to outwardly; freely flowering habit with about 200 flowers developing per inflorescence and about 25,000 flowers developing per plant during the flowering season; flowers sessile.

*Natural flowering season*.—Long flowering habit, plants flower from the late spring into September in The Netherlands.

*Postproduction longevity*.—Good postproduction longevity, flowers maintain good substance for about 20 days as a cut flower; flowers not persistent.

*Fragrance*.—None detected.

*Flower buds*.—Length: About 1.6 cm. Diameter: About 2.5 mm. Shape: Narrowly oblanceolate; curved. Texture and luster: Densely pubescent; matte. Color: Close to N79A; towards the base, close to N79C; immature calyx, close to 187A, fading towards the base to close to 150D.

*Inflorescence height*.—About 5.6 cm.

*Inflorescence diameter*.—About 8.4 cm.

*Flower length* (*vertical*).—About 2 cm.

*Flower diameter* (*horizontal*).—About 6 mm.

*Flower depth* (*height*).—About 3.7 cm.

*Petals*.—Arrangement: Labiate; upper lip hooded; lower lip, a single lobe; lips fused 60% of total length. Length, upper lip: About 3.1 cm. Length, lower lip: About 3.5 cm. Width, upper lip: About 1.5 mm. Width, lower lip: About 6 mm. Shape, upper lip: Lanceolate; apex, obtuse. Shape, lower lip: Oblanceolate; apex, three-parted. Margin, upper and lower lips: Entire; lower petal, slightly undulate. Texture and luster, upper and lower lips, upper surface: Smooth, glabrous; velvety; matte. Texture and luster, upper and lower lips, lower surface: Moderately pubescent; moderately velvety; matte. Color, upper lip: When opening and fully opened, upper surface: Close to N79C; color does not fade with development. When opening and fully opened, lower surface: Close to N79C; color does not fade with development. Color, lower lip: When opening, upper surface: Close to N79C. When opening, lower surface: Close to N79B to N79C. Fully opened, upper surface: Close to between NN78A and N79C; color does not fade with development. Fully opened, lower surface: Close to N79B to N79C; color does not fade with development.

*Sepals*.—Quantity and arrangement: Five in a single whorl; lower 90% fused into a tubular calyx. Length: About 9 mm. Width: About 0.8 mm. Apex: Acute. Margin: Free parts, entire. Texture and luster, upper surface: Smooth and mostly glabrous; upper margin, moderately pubescent; matte. Texture and luster, lower surface: Smooth, glabrous; slightly glossy. Color: When opening and fully opened, upper surface: Close to 182D. When opening and fully opened, lower surface: Close to 187A fading towards the base to close to 150D.

*Inflorescence bracts*.—Quantity and arrangement: About 70 at the base of inflorescence; smaller upper bracts, about 60 in number, are arranged in numerous whorls and are subtended by the larger lower ten bracts arranged in a single whorl. Length, upper bracts: About 1.3 cm. Length, lower bracts: About 3.7 cm. Width, upper bracts: About 1 mm. Width, lower bracts: About 2 cm. Shape, upper bracts: Lanceolate; apex, apiculate and base, cuneate. Shape, lower bracts: Ovate; apex, apiculate and base, cuneate. Margin, upper and lower bracts: Entire. Texture, upper and lower bracts, upper surface: Smooth, glabrous. Texture, upper and lower bracts, lower surface: Sparsely pubescent. Color, upper bracts, upper and lower surfaces: Close to N77B. Color, lower bracts, upper surface: Close to NN137A; main vein tinged with close to 70A. Color, lower bracts, lower surface: Close to 138A.

*Reproductive organs*.—Stamens: Quantity per flower: Two. Filament length: About 1.8 cm. Filament color: Close to N74C fading towards the base to close to 73D. Anther size: About 2 mm by 0.5 mm. Anther shape: Narrowly elliptic; dorsifixed. Anther color: Close to 70A. Pollen amount: Scarce. Pollen color: Close to 11D. Pistils: Quantity per flower: One. Pistil length: About 3.6 cm. Stigma diameter: About 0.5 mm. Stigma shape: Cleft, unequal. Stigma color: Close to N77A. Style length: About 3.4 cm. Style color: Close to N78B. Ovary color: Close to 152D.

*Seed and fruit*.—Seed and fruit production have not been observed on plants of the new *Monarda* to date.

Disease & pest resistance: Plants of the new *Monarda* not been observed to be resistant to pathogens and pests common to *Monarda* plants to date.

Garden performance: Plants of the new *Monarda* have exhibited good tolerance to rain, wind and high temperatures about 40° C. and to be suitable for USDA Hardiness Zones 5 to 10.

It is claimed:

1. A new and distinct *Monarda* plant named 'Allvin' as illustrated and described.

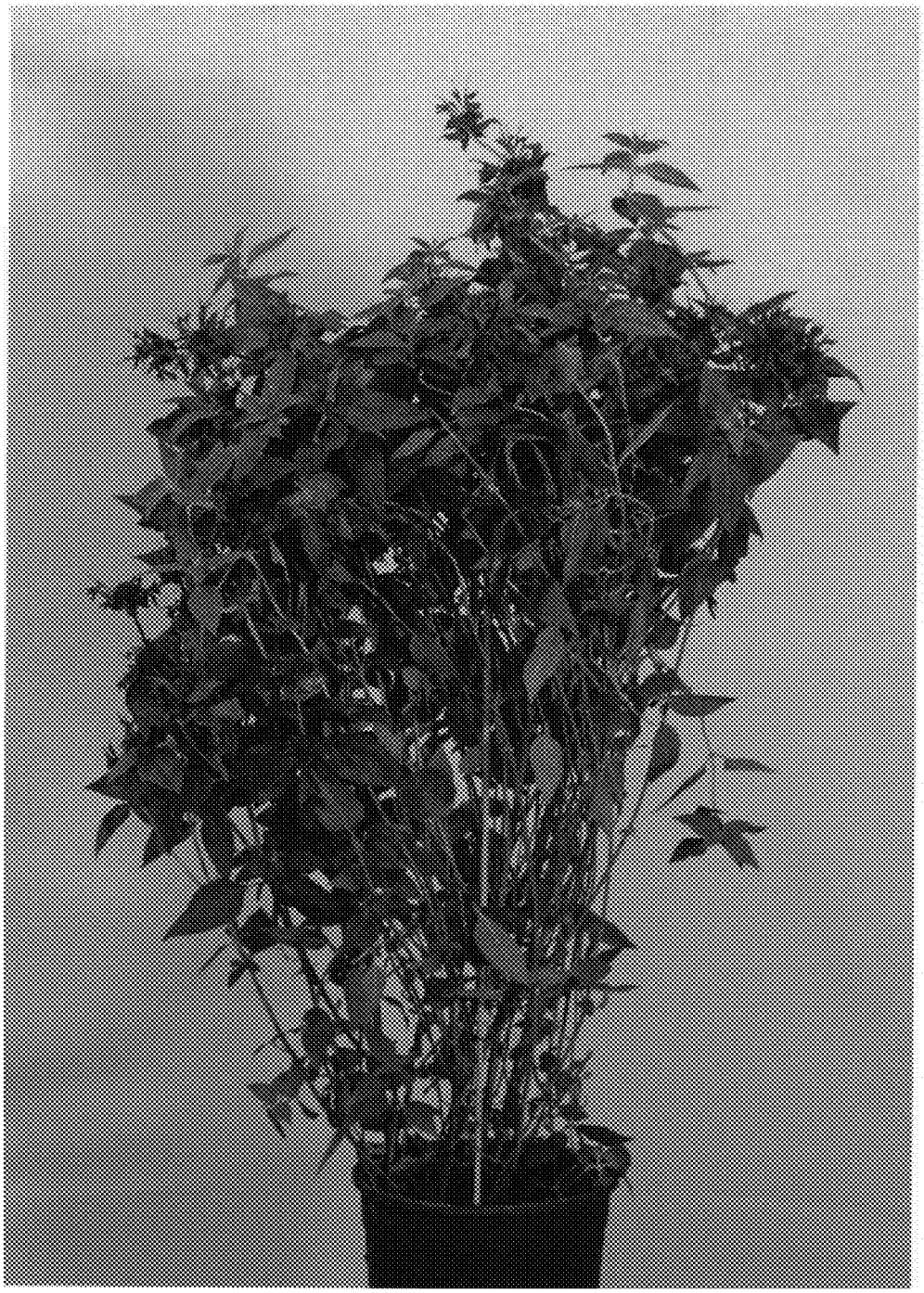

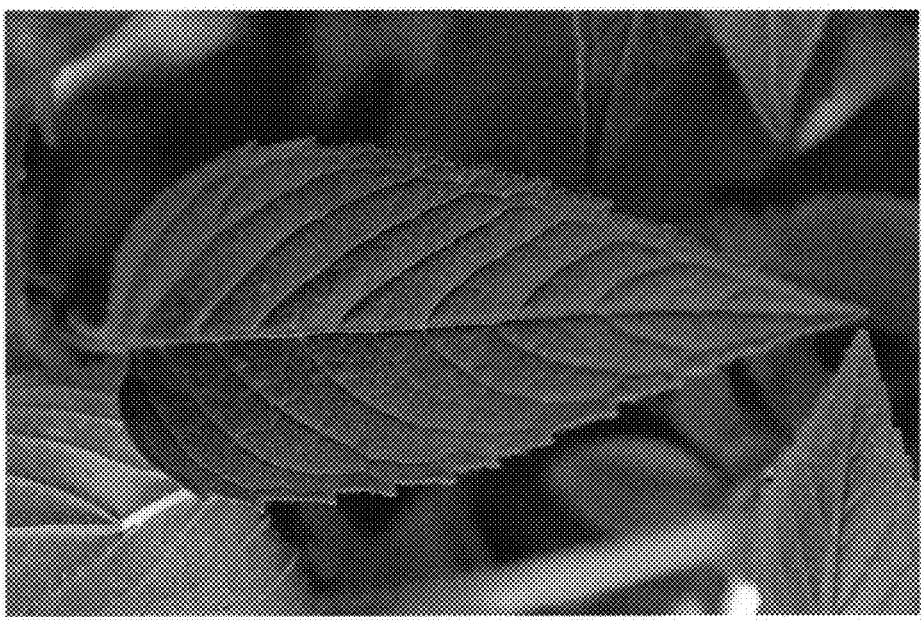
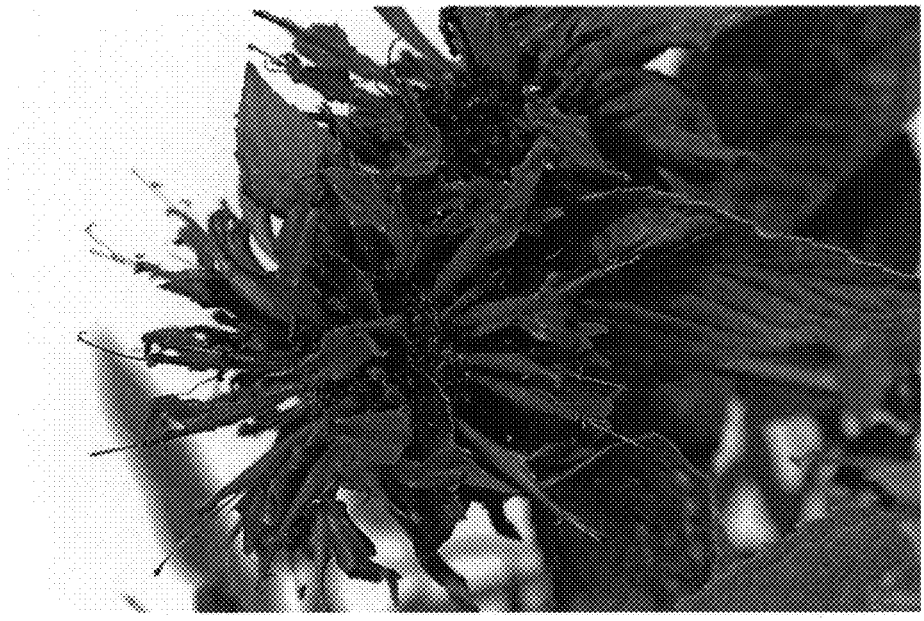

* * * * *